United States Patent
Buelow et al.

(10) Patent No.: US 9,980,692 B2
(45) Date of Patent: May 29, 2018

(54) SYSTEM AND METHOD FOR INTERACTIVE ANNOTATION OF AN IMAGE USING MARKER PLACEMENT COMMAND WITH ALGORITHM DETERMINING MATCH DEGREES

(71) Applicant: KONINKLIJKE PHILIPS N.V., Eindhoven (NL)

(72) Inventors: Thomas Buelow, Hamburg (DE); Kirsten Regina Meetz, Hamburg (DE); Martin Bergtholdt, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 523 days.

(21) Appl. No.: 14/356,394

(22) PCT Filed: Oct. 30, 2012

(86) PCT No.: PCT/IB2012/055997
§ 371 (c)(1),
(2) Date: May 6, 2014

(87) PCT Pub. No.: WO2013/068881
PCT Pub. Date: May 16, 2013

(65) Prior Publication Data
US 2014/0289605 A1 Sep. 25, 2014

Related U.S. Application Data

(60) Provisional application No. 61/557,008, filed on Nov. 8, 2011.

(51) Int. Cl.
*A61B 6/00* (2006.01)
*G06F 19/24* (2011.01)
(Continued)

(52) U.S. Cl.
CPC ............ *A61B 6/468* (2013.01); *A61B 5/7475* (2013.01); *A61B 8/468* (2013.01); *G03F 9/7069* (2013.01);
(Continued)

(58) Field of Classification Search
CPC ... G06F 17/241; G06F 17/242; G06F 17/2247
(Continued)

(56) References Cited

U.S. PATENT DOCUMENTS 6,480,813 B1 11/2002 Bloomquist et al.
2003/0088178 A1* 5/2003 Owens ................... A61B 90/36
600/420

(Continued)

FOREIGN PATENT DOCUMENTS

JP 2003534060 A 11/2003
JP 2004180987 A 7/2004
(Continued)

OTHER PUBLICATIONS

Bonneau, P. et al. "Man machine cooperation for 3D objects pose estimation", Systems, Man and Cybernetics, Conference Proceedings, Oct. 17-20, 1993, pp. 294-299, vol. 2.
(Continued)

*Primary Examiner* — Cesar B Paula
*Assistant Examiner* — Luu-Phuong Nguyen

(57) ABSTRACT

A system 100 for enabling interactive annotation of an image 102, comprising a user input 160 for receiving a placement command 162 from a user, the placement command being indicative of a first placement location of a marker 140 in the image 102, and a processor 180 arranged for (i) applying an image processing algorithm to a region 130 in the image, the region being based on the first placement location, and the image processing algorithm being responsive to image portions which visually corre-
(Continued)

spond to the marker 140 for establishing a plurality of match degrees between, on the one hand, the marker, and, on the other hand, a plurality of image portions within the region, (ii) establishing a second placement location in dependence on the plurality of match degrees and the respective plurality of image portions for matching the marker 140 to the region in the image, and (iii) placing the marker 140 at the second placement location in the image 102.

20 Claims, 5 Drawing Sheets

(51) Int. Cl.
| | | |
|---|---|---|
| G06F 3/01 | (2006.01) | |
| G03F 9/00 | (2006.01) | |
| A61B 5/00 | (2006.01) | |
| A61B 8/00 | (2006.01) | |
| G06F 3/0484 | (2013.01) | |
| G06F 17/24 | (2006.01) | |
| G06T 7/73 | (2017.01) | |
| G06F 17/22 | (2006.01) | |

(52) U.S. Cl.
CPC .......... G06F 3/011 (2013.01); G06F 3/04845 (2013.01); G06F 17/241 (2013.01); G06F 19/24 (2013.01); G06T 7/74 (2017.01); *G03F 9/7088* (2013.01); *G06F 17/2247* (2013.01); *G06F 17/242* (2013.01); *G06F 17/243* (2013.01); *G06T 2207/10116* (2013.01); *G06T 2207/20012* (2013.01); *G06T 2207/20096* (2013.01); *G06T 2207/20101* (2013.01); *G06T 2207/30068* (2013.01); *G06T 2207/30204* (2013.01)

(58) Field of Classification Search
USPC ........................................................ 715/232
See application file for complete search history.

(56) References Cited

U.S. PATENT DOCUMENTS

| | | |
|---|---|---|
| 2005/0180636 A1 | 8/2005 | Iizuka |
| 2007/0174769 A1 | 7/2007 | Nyez |
| 2008/0118156 A1* | 5/2008 | Okada ................ G06K 9/00228 382/195 |
| 2009/0324049 A1 | 12/2009 | Kontos et al. |
| 2010/0004539 A1 | 1/2010 | Chen et al. |
| 2010/0114537 A1* | 5/2010 | Pershing ............. G06F 17/5004 703/1 |
| 2010/0145373 A1 | 6/2010 | Alon |
| 2011/0182493 A1* | 7/2011 | Huber ................. G06F 19/3487 382/132 |
| 2011/0185316 A1 | 7/2011 | Reid et al. |
| 2012/0088981 A1* | 4/2012 | Liu ...................... G06K 9/6215 600/300 |
| 2015/0196201 A1* | 7/2015 | Andersson |
| | | Engels ............... G01N 21/4795 600/431 |

FOREIGN PATENT DOCUMENTS

| | | |
|---|---|---|
| JP | 2007307358 A | 11/2007 |
| JP | 2007536666 A | 12/2007 |
| WO | 0063844 A1 | 10/2000 |
| WO | 2007135913 A1 | 11/2007 |
| WO | 2008052312 A1 | 5/2008 |
| WO | 2010052598 A1 | 5/2010 |

OTHER PUBLICATIONS

Seung-Ran, P. et al. "Semi-automatic road extraction algorithm from IKONOS images using template matching". 22nd Asian Conference on Remote Sensing, vol. 5, Nov. 5, 2001.

Gleicher, M. "Image Snapping". Computer Graphics Proceedings, Los Angeles, CA, Aug. 6-11, 1995, pp. 183-190.

Venolia, D. "Facile 3D Direct Manipulation". Proceedings CHI'93 Proceedings of the INTERACT '93 and CHI '93 Conference on Human Factors in Computing Systems, pp. 31-36.

Maass, S. et al. "Efficient View Management for Dynamic Annotation Placement in Virtual Landscapes". Smart Graphic, 6th International Symposium, SG 2006, Vancouver, Canada, p. 1-12.

* cited by examiner

SYSTEM AND METHOD FOR INTERACTIVE ANNOTATION OF AN IMAGE USING MARKER PLACEMENT COMMAND WITH ALGORITHM DETERMINING MATCH DEGREES

This application is a national stage application under 35 U.S.C. § 371 of International Application No. PCT/IB2012/055997 filed on Oct. 30, 2012 and published in the English language on May 16, 2013 as International Publication No. WO/2013/068881, which claims priority to U.S. Application No. 61/557,008 filed on Nov. 8, 2011, the entire disclosures of which are incorporated herein by reference.

FIELD OF THE INVENTION

The invention relates to a system and a method for enabling interactive annotation of an image. The invention further relates to a workstation and an imaging apparatus comprising the system set forth, and to a computer program product comprising instructions for causing a processor system to perform the method set forth.

BACKGROUND OF THE INVENTION

Image annotation refers to a process in which specific areas of an image are marked by adding text, color overlays, etc. In particular, graphical annotations such as curves, lines, symbols, etc., henceforth referred to as markers, may be added. It is known to annotate images by hand, e.g., using a pen or a pencil. Moreover, it is known to use a system to annotate images in an interactive manner. In such a system, the user may operate a user interface device such as a mouse to draw or drag markers on a displayed image, and in response, the system draws or places the markers accordingly on the displayed image.

US 2007/0174769 A1 describes a system and a method for enhancing the delivery and display of medical images for preoperative planning and diagnosis. It is said that a user may select an initial annotation, operate the system to modify the initial annotation along the displayed image in association with anatomical features, and then fix the appropriate annotation at the desired location on the displayed image for later reference.

Moreover, in reference to labeling vertebrae, it is disclosed that the system may be used to automatically label vertebrae. Specifically, a user may select an initial annotation and associate it with a vertebra. Once this is done, the system will automatically label the remaining vertebrae extending superiorly and inferiorly from the initial reference vertebrae as they were previously mapped by the machine reader.

A problem of the above system is that it is inconvenient for the user to accurately place an annotation at a desired location in the displayed image.

SUMMARY OF THE INVENTION

It would be advantageous to have a system or a method for enabling a user to accurately place a marker at a desired location in an image in a more convenient manner.

To better address this concern, a first aspect of the invention provides a system for enabling interactive annotation of an image, the system comprising:
a user input for receiving a placement command from a user, the placement command being indicative of a first placement location of a marker in the image, and
a processor arranged for (i) applying an image processing algorithm to a region in the image, the region being based on the first placement location, and the image processing algorithm being responsive to image portions which visually correspond to the marker for establishing a plurality of match degrees between, on the one hand, the marker, and, on the other hand, a plurality of image portions within the region, (ii) establishing a second placement location in dependence on the plurality of match degrees and the respective plurality of image portions for matching the marker to the region in the image, and (iii) placing the marker at the second placement location in the image.

In a further aspect of the invention, a workstation and an imaging apparatus is provided comprising the system set forth.

In a further aspect of the invention, a method is provided for enabling interactive annotation of an image, the method comprising:
receiving a placement command from a user, the placement command being indicative of a first placement location of a marker in the image,
applying an image processing algorithm to a region in the image, the region being based on the first placement location, and the image processing algorithm being responsive to image portions which visually correspond to the marker for establishing a plurality of match degrees between, on the one hand, the marker, and, on the other hand, a plurality of image portions within the region,
establishing a second placement location in dependence on the plurality of match degrees and the respective plurality of image portions for matching the marker to the region in the image, and
placing the marker at the second placement location in the image.

In a further aspect of the invention, a computer program product is provided comprising instructions for causing a processor system to perform the method set forth.

The above measures enable a user to interactively annotate the image. For that purpose, a placement command is received from the user. The placement command is indicative of a location, i.e., the first placement location, where the user places a marker in the image. Then, for each of a plurality of image portions within a region based on the first placement location, a match degree is determined between the marker and the respective image portion. The match degree indicates how well the marker resembles the respective image portion, and thus represents their visual correspondence. For determining the match degree, an image processing algorithm is used that is responsive to image portions that visually correspond to the marker, i.e., it provides a distinct output for said image portions and thus allows said image portions to be identified. A second placement location is then determined using the plurality of match degrees and the plurality of image portions for matching the marker to the region in the image. Finally, the marker is placed at the second placement location within the image rather than at the first placement location.

The above measures have the effect that when a user indicates a first or initial placement location of a marker in an image, the first placement location is refined by matching, within a region that is based on the first placement location, a number of image portions to the marker, with a second or final placement location being determined based on the outcome of said matching. Therefore, information on how well the marker matches certain image portions is used in determining where to place the marker within the region.

The invention is partially based on the recognition that a marker is frequently predictive of the image portion that is to be annotated since the marker often visually resembles the image portion. A reason for this is that a marker may be application specific, i.e., its appearance may be tailored to the type of image being annotated. For example, when annotating anatomic landmarks in 2D mammograms, the mammilla or the inframammary fold is typically marked using a point whereas the pectoralis muscle is typically marked using a straight line segment. The appearance of the marker is thus often predictive of the image portion that is to be annotated. As a result, the appearance of the marker provides implicit information on where the marker is to be placed within the image, e.g., near or on an image portion resembling the marker. The present invention employs said recognition by allowing a user to indicate a first placement location of the marker, and then said first placement location is used to match the marker to a plurality of image portions, and finally the outcome of the matching is used to determine a second placement location for the marker.

Advantageously, the user does not need to place the marker with a high degree of accuracy in the image since the placement location is automatically refined, resulting in a more accurate placement location of the marker. Consequently, the user can place the marker more rapidly, because he knows that the marker does not have to be placed with a high degree of accuracy Optionally, the user input is arranged for receiving a selection command from the user, the selection command being indicative of a selection of the marker amongst a plurality of different markers, and the processor is arranged for configuring the image processing algorithm in dependence on the selected marker so as to be responsive to image portions which visually correspond to the selected marker.

When the user can select the marker amongst a plurality of different makers, the user will typically tailor his selection to the image portion that is to be annotated. By receiving the selection command from the user, it is known which marker is selected amongst the plurality of different markers. In response thereto, the processor configures the image processing algorithm to be responsive to image portions that visually correspond to the selected marker. Hence, the selection of the marker is automatically taken into account in the refinement of the placement location by customizing the image processing algorithm to the selected marker.

Optionally, the selection command is further indicative of an orientation of the selected marker as determined by the user, and wherein the processor is further arranged for configuring the image processing algorithm in dependence on the orientation so as to be responsive to image portions which visually correspond to the selected marker having said orientation.

When the user can determine the orientation of the marker, the user will typically select or adjust the orientation so as to correspond to the expected orientation of the image portion that is to be annotated. By receiving said selection command from the user, the orientation of the selected marker, as determined by the user, is known. In response, the processor configures the image processing algorithm to be responsive to image portions that visually correspond to the selected marker having the particular orientation. Hence, the orientation of the marker is automatically taken into account in the refinement of its placement location by customizing the image processing algorithm accordingly.

Optionally, the user input is arranged for receiving type data, the type data being indicative of a type of image portion to be annotated in the image, and the processor is further arranged for configuring the image processing algorithm in dependence on the type data so as to be responsive to image portions which visually correspond to the type of image portion and the marker.

When a user can explicitly indicate a type of image portion that is to be annotated in the image, e.g., a pectoralis muscle, this information may be used in addition to the appearance of the marker in determining the placement location of the marker. By receiving type data that is indicative of the type of image portion that is to be annotated and configuring the image processing algorithm to be responsive to the type of image portion, the type of image portion, in addition to the marker itself, is taken into account in the refinement of the placement location of the marker.

Optionally, said placing of the marker comprises adjusting at least one of: a shape, an orientation and a size of the marker for matching the marker to an image portion at the second placement location. The appearance of the marker typically corresponds to an expected appearance of the image portion that is to be annotated. In practice, the actual appearance of the image portion may deviate from the expected appearance. In such a case, an improved annotation is obtained by adjusting, after having determined the placement location of the marker, the appearance of the marker with respect to the image portion at the second placement location and placing the marker after said adjustment.

Optionally, the processor is arranged for establishing the plurality of match degrees by establishing a plurality of distances between, on the one hand, the first placement location and, on the other hand, the respective plurality of image portions, and weighting the plurality of match degrees with the plurality of distances for promoting image portions located nearer to the first placement location.

The first placement location, as provided by the user, is indicative of where the user knows or expects that the image portion that is to be annotated is located. Hence, when refining the placement location, it is desirable not to deviate too much from the first placement location because the likelihood of finding said image portion decreases with increasing distance from the first placement location. By weighting each match degree with a distance of the respective image portion to the first placement location, the above recognition is taken into account. As such, a trade-off is obtained between the resemblance of an image portion to the marker and its distance to the first placement location.

Optionally, the processor is arranged for establishing the plurality of match degrees by establishing a plurality of detail measures being indicative of image detail present in the image between, on the one hand, the first placement location, and on the other hand, the respective plurality of image portions, and weighting the plurality of match degrees with the plurality of detail measures for promoting image portions having less image detail in the image between them and the first placement location.

When image detail is present near the image portion that is to be annotated, the user must take care to place the marker correctly with respect to the image detail. A reason for this is that image detail provides a point of reference. Thus, the first placement location is expected to be accurate with respect to the image detail, and hence accurate in the direction of the image detail. This recognition is taken into account by the abovementioned measures, which result in detail being present between the first placement location and an image portion acting as a kind of barrier, in that the match degree of said image portion is lowered or devaluated. Consequently, the second placement location is likely to deviate less from the first placement location in directions in which the latter location is expected to be accurate, and more in directions in which said location may be inaccurate.

Optionally, the processor is arranged for establishing the second placement location by using a force-based model comprising the plurality of match degrees as attracting forces. A force-based model constitutes an efficient manner for establishing the second placement location in dependence on the plurality of match degrees.

Optionally, the user input is arranged for receiving range data from the user, the range data being indicative of a size of the region, and the processor being arranged for establishing the size of the region in dependence on the range data. The user can thus influence the size of the region, e.g., in order to decrease the size of the region when the first placement location is expected to be accurate, or to increase the size of the region when the first placement location is not expected to be accurate.

Optionally, the placement command is further indicative of a placement direction at a time of providing the placement command, and the processor is arranged for establishing a shape of the region with respect to the first placement location in dependence on the placement direction. The user can thus influence the shape of the region with respect to the first placement location via the placement direction when providing the placement command. The placement direction may be, e.g., a direction corresponding to the physical movement of a user interface device, e.g., a mouse, or a direction of the displayed movement of a cursor on a display, etc. Advantageously, when the user provides the placement command before an intended placement location has been reached, the system may compensate for said fact by predominantly shaping the region in the placement direction.

Optionally, the placement command is further indicative of a placement speed at the time of providing the placement command, and the processor is further arranged for establishing a size of the region in dependence on the placement speed. The user can thus influence the size of the region with the placement speed when providing the placement command. The placement speed may be, e.g., a speed corresponding to the physical movement of a user interface device, or a speed of the displayed movement of a cursor on a display, etc. Advantageously, the placement direction and placement speed may be combined to simulate inertia of the user interface device or of the cursor for offering the user an intuitive manner of influencing the shape and size of the region.

It will be appreciated by those skilled in the art that two or more of the above-mentioned embodiments, implementations, and/or aspects of the invention may be combined in any way deemed useful.

Modifications and variations of the imaging apparatus, the workstation, the method, and/or the computer program product, which correspond to the described modifications and variations of the system, can be carried out by a person skilled in the art on the basis of the present description.

A person skilled in the art will appreciate that the method may be applied to multi-dimensional image data, e.g. two-dimensional (2-D), three-dimensional (3-D) or four-dimensional (4-D) images. A dimension of the multi-dimensional image data may relate to time. For example, a three-dimensional image may comprise a time domain series of two-dimensional images. The image may be a medical image, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM). However, the image may also be of any other type, e.g., a cartographic or seismic image which the user wishes to annotate.

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1:
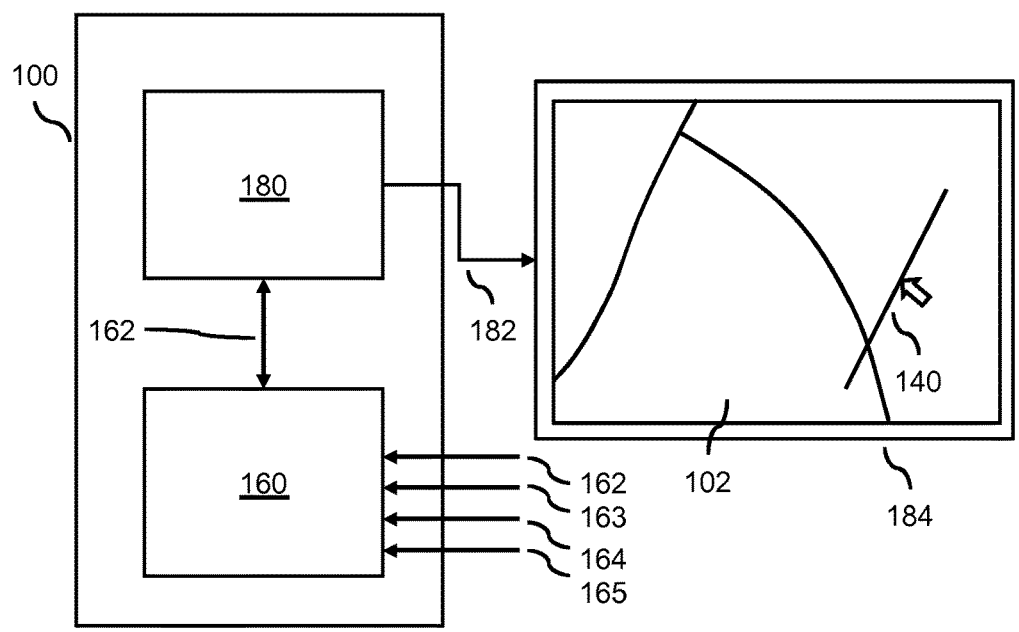
FIG. 1 shows a system according to the present invention and a display.

FIG. 1 shows a system 100 for enabling interactive annotation of an image 102. The system 100 comprises a user input 160 for receiving a placement command 162 from a user, with the placement command 162 being indicative of a first placement location of a marker in the image 102 for enabling the user to place the marker in the image 102. Although not shown in FIG. 1, the user input 160 may be connected to a user interface device such as a mouse, keyboard or touch screen, which is operated by the user. The system 100 further comprises a processor 180. The processor 180 may be arranged for establishing a region in the image in dependence on the first placement location. For that purpose, the processor 180 is shown to be connected to the user input 160 for receiving the placement command 162. The processor 180 is further arranged for applying an image processing algorithm to the region, the image processing algorithm being responsive to image portions which visually correspond to the marker for establishing a plurality of match degrees between, on the one hand, the marker, and, on the other hand, a plurality of image portions within the region. Moreover, the processor 180 is arranged for placing the marker at the second placement location in the image 102. FIG. 1 shows the processor 180 arranged for placing the marker by being connected to a display 184 displaying the marker at the second placement location in the image 102. For that purpose, the processor 180 provides display data 182 to the display 184. Alternatively, or additionally, the processor 180 may place the marker by creating association data which may be used by, e.g., an image display device to display the marker at the second placement location in the image 102.

Figure 2:
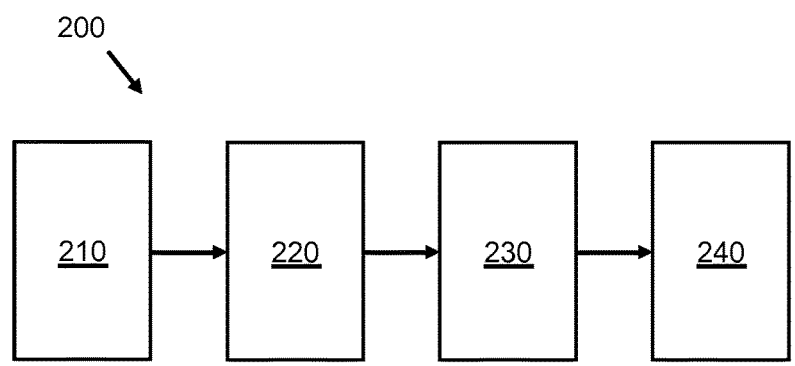
FIG. 2 shows a method according to the present invention.

FIG. 2 shows a method 200 of enabling interactive annotation of an image, the method comprising a first step 210 titled "OBTAINING FIRST PLACEMENT LOCATION", the first step 210 comprising receiving a placement command from a user, the placement command being indicative of a first placement location of a marker in the image. The method further comprises a second step 220 titled "MATCHING MARKER TO IMAGE PORTIONS WITHIN A REGION" comprising applying an image processing algorithm to a region in the image, the region being based on the first placement location, and the image processing algorithm being responsive to image portions which visually correspond to the marker for establishing a plurality of match degrees between, on the one hand, the marker, and, on the other hand, a plurality of image portions within the region. The method further comprises a third step 230 titled "ESTABLISHING SECOND PLACEMENT LOCATION" comprising establishing a second placement location in dependence on the plurality of match degrees and the respective plurality of image portions for matching the marker to the region in the image. The method further comprises a fourth step 240 titled "PLACING THE MARKER AT SECOND PLACEMENT LOCATION" comprising placing the marker at the second placement location in the image.

The method 200 may correspond to an operation of the system 100, and will be further explained in reference to the system 100. It will be appreciated, however, that the method may be performed independently of said system, e.g., by another system or device.

Figure 3A:
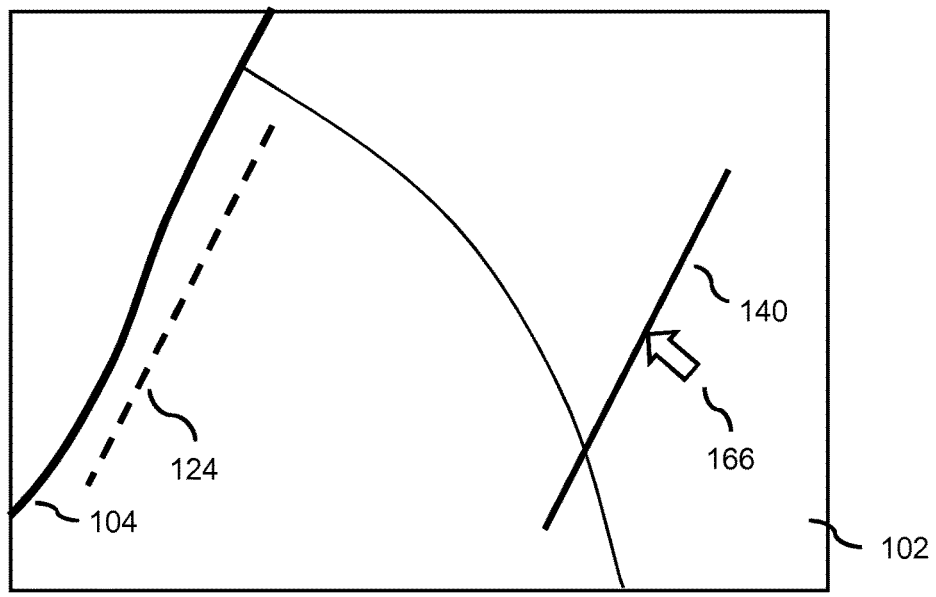
FIG. 3a shows the user moving a marker over an image.

FIG. 3a and further figures illustrate an operation of the system 100 by showing an exemplary display of the image 102 and marker 140 on the display 184. FIG. 3a shows the image 102 being a medical image, the medical image being a mammogram showing the pectoral muscle 104 and an outline of the breast. The mammogram may be used, amongst others, to assess the quality of patient positioning in mammography. For that purpose, a user such as a radiologist or a technician may need to annotate the mammogram by placing simple geometric primitives, such as points or lines, on an anatomic landmark in the mammogram. In the example of FIG. 3a, the user wishes to place a marker 140 being a line segment on the pectoral muscle 104 in order to annotate or mark the pectoral muscle 104.

The system 100 may be arranged for allowing the user to control a cursor 166 displayed over the image in order move the marker 140. It will be appreciated, however, that this functionality may also be provided by another system or device instead of the system 100. Moreover, when placing the marker, only the cursor 166 may be displayed, i.e., without the marker 140, or only the marker 140 may be displayed, i.e., without the cursor 166.

Figure 3B:
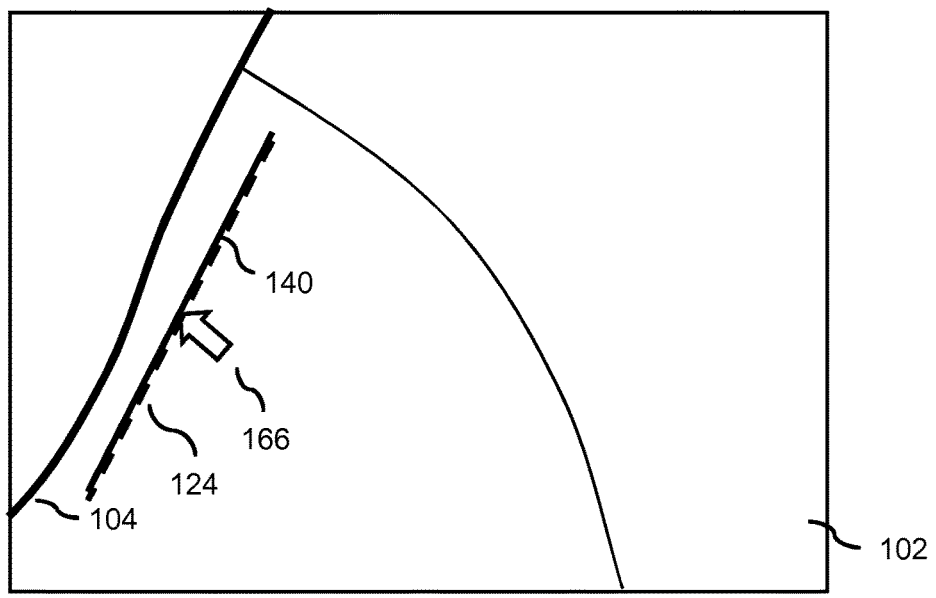
FIG. 3b shows the user placing the marker at a first placement location.

FIG. 3a further shows a first placement location 124 being a location where the user wishes to place the marker 140, the first placement location 124 being near the pectoral muscle 104 in order to annotate or mark the pectoral muscle 104. For that purpose, the user may move the cursor 166, e.g., by using the aforementioned user interface device, and may provide a placement command, e.g., by pressing or releasing a button of the aforementioned user interface device, thereby indicating the wish to place the marker 140 at the present location of the cursor 166. FIG. 3b shows a result of the above actions of the user, i.e., the user having moved the cursor 166 and thus the marker 140 to the first placement location 124. The user may at this time or in this situation provide the placement command, thereby indicating the wish to place the marker 140 at the first placement location 124.

FIGS. 3a and 3b both show that the placement location 124 is adjacent to the pectoral muscle 104 but nevertheless beside the pectoral muscle 104. Thus, placement of the marker 140 at the first placement location 124 would result in misalignment between the marker 140 and the pectoral muscle 104. This may result in a non-perfect, possibly even non-adequate annotation of the pectoral muscle 104. The user may be aware of the misalignment, but may nevertheless choose said placement location due to, e.g., time constraints or difficulty in accurately placing the marker. The user may also be unaware of the misalignment, e.g., because he is not able to easily perceive said misalignment.

Figure 3C:
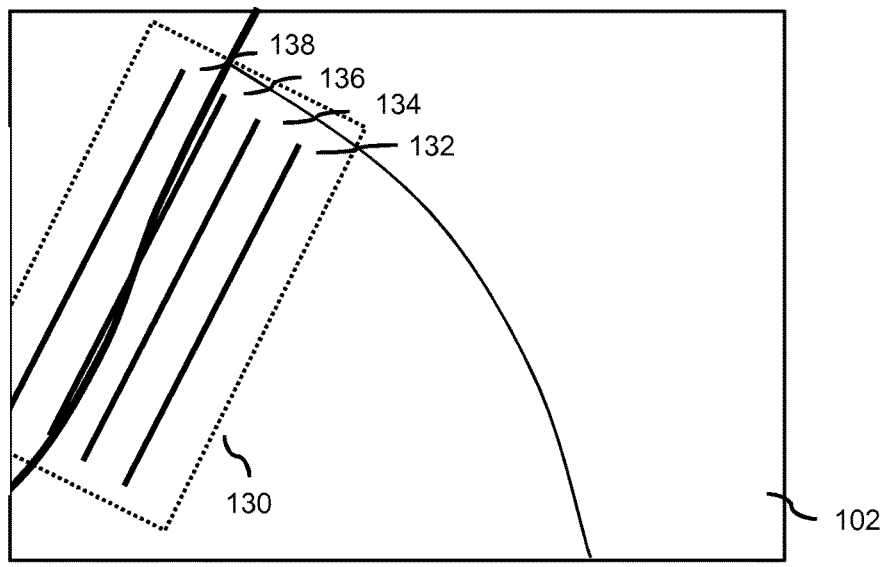
FIG. 3c shows a region and a plurality of image portions within the region.

FIG. 3c illustratively shows an intermediate step in the operation of the system 100, which may typically not be shown to the user. For ease of illustration, the cursor 166 and marker 140 have been omitted in FIG. 3c, as well as reference signs indicating the pectoral muscle 104. FIG. 3c shows the processor 180 having established a region 130 in the image 102 in dependence on the first placement location 124. When comparing FIG. 3b with FIG. 3c, it can be seen that the region 130 is located approximately around the first placement location 124. Also shown are a plurality of image portions 132, 134, 136, 138 within the region 130, the image portions being the portions of the image 102 that underlie each of the lines, i.e., are delineated by each of the lines. These image portions 132, 134, 136, 138 have the same shape as the marker 140 and represent a plurality of potential placement locations of the marker 140, the placement locations being co-located with the image portions and thus are not explicitly shown. As is shown in FIG. 3c, one of the plurality of image portions 134 corresponds to the portion of the image 102 at the first placement location 124.

It is noted that, for the sake of clarity, the image portions 132, 134, 136, 138 shown in FIG. 3c are limited in number, distinct and non-overlapping. It will be appreciated, however, that the image portions may also be immediately adjacent and/or partially overlapping. In particular, the image portions 132, 134, 136, 138 may be constituted by all or substantially all potential placement locations within the region 130.

It is noted that, consequently, the processor 180 may not need to be arranged for explicitly establishing the region 130 based on the first placement location 124. The region 130 rather may be an implicit result of, e.g., the image processing algorithm having located the plurality of image portions in the image. The region 130 may also be an implicit result of the processor 180 modifying one or more parameters of the image processing algorithm, e.g., by restricting or constraining the image processing algorithm to a maximum number of iterations. The processor 180 may also be arranged for explicitly establishing the region 130 in the image. For example, the processor 180 may be arranged for determining the region 130 in dependence on the proximity to the first placement location 124. Thus, the region may be constituted by all image portions which have at least a given proximity to the first placement location 124. The region 130 may also be established by simply defining a circle, rectangle or any other geometrical shape around the first placement location 124. The shape of the region 130 may be chosen to be larger in a certain direction. For example, when the marker 140 has a certain predominant orientation, the shape of the region 130 may be larger in a direction perpendicular to the predominant orientation than in other directions.

After having established the region 130 in the image, the processor 180 applies an image processing algorithm to the region 130 for establishing a match degree between, on the one hand, the marker 140, and, on the other hand, the plurality of image portions 132, 134, 136, 138 within the region. The match degree is established to determine how well the marker 140 would match each of the image portions 132, 134, 136, 138 if the marker 140 were placed on top of the respective image portion, i.e., at a corresponding placement location. In this particular example, with the marker 140 being a line segment, the image processing algorithm would establish how much each of the image portions 132, 134, 136, 138 resembles a line segment as constituted by the marker 140.

The image processing algorithm may be any image processing algorithm known from the field of image processing that is suitable for determining a match degree or visual correspondence between the marker 140 and an image portion 132, 134, 136, 138. The image processing algorithm may comprise determining a luminance difference between each of the plurality of image portions 132, 134, 136, 138 and an image representation of the marker 140. The luminance difference may be a difference between pixels of the image portions 132, 134, 136, 138 and corresponding pixels of the image representation of the marker 140. A small luminance difference between pixels may indicate a high match degree, i.e., a high visual correspondence, and a large luminance difference may indicate a low match degree, i.e., low visual correspondence. It will be appreciated, however, that the field of image processing comprises many other algorithms that may be used for said purpose.

For example, a so-termed feature enhanced image may be computed from the image 102 and the marker 140, the feature enhancement image indicating the match degree between the marker 140 and each of the image portions 132, 134, 136, 138 within the region. For example, when the marker 140 is a point label, the image processing algorithm may compute a feature enhanced image in which point-like or blob-like features are enhanced. The enhancement may be performed in various ways. For example, a blob feature enhancement image may be derived from the Hessian matrix computed for each pixel within the region 130. Here, the magnitude of the smallest, in terms of absolute value, Eigen value of the Hessian matrix may be interpreted as the so-termed blob feature indicating said match degree. Similarly, when the marker 140 is a line segment, the image processing algorithm may compute a feature enhanced image in which line or edge features are enhanced, for example by interpreting a high second smallest Eigen value and a low smallest Eigen value in said Hessian matrix as the line or edge feature. Alternatively, or additionally, Gabor filters, Hough transforms or any other suitable technique may be used.

Having established the match degree between, on the one hand, the marker 140, and, on the other hand, a plurality of image portions 132, 134, 136, 138 within the region 130, the processor 180 may establish a second placement location 126 in dependence on the plurality of match degrees and the respective plurality of image portions. For example, the processor 180 may establish the second placement location 126 as a location of one of the plurality of image portions 136 having a highest one of the plurality of match degrees.

Figure 3D:
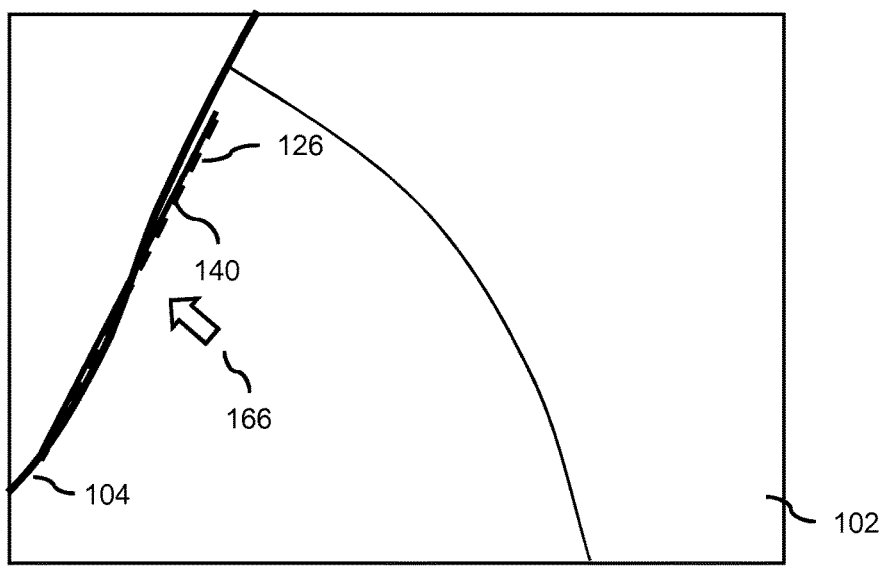
FIG. 3d shows the system placing the marker at a second placement location.

FIG. 3c shows an example of the image portion 136 being approximately constituted by the pectoral muscle 104 and having the highest one of the plurality of match degrees. Moreover, in this example, the location of said image portion 136 is established as the second placement location 126. The result of this operation is shown in FIG. 3d, where the marker 140 is shown to be placed at the second placement location 126.

Although not shown in any of the previous figures, the processor may also be arranged for establishing the plurality of match degrees by establishing a plurality of distances between, on the one hand, the first placement location, and on the other hand, the respective plurality of image portions, and weighting the plurality of match degrees with the plurality of distances for promoting image portions that are located nearer to the first placement location. Therefore, the processor does not necessarily select the location of the one of the plurality of image portions most resembling the marker as the second placement location, but rather a location of an image portion that reasonably resembles the marker and is located nearer to the first placement location than said image portion most resembling the marker. The weighting may comprise multiplying the match degree by a weighting factor in accordance with the distance. The weighting may also comprise adding or subtracting the distance to or from the match degree. It will be appreciated that various other mechanisms may be used as well for promoting image portions that are located close to the first placement location over image portions being located farther away from the first placement location.

Moreover, the processor may be arranged for establishing the second placement location by using a force-based model comprising the plurality of match degrees as attracting forces. In addition, the plurality of distances may be comprised in the force-based model as repelling forces. The location of an image portion at equilibrium or being subjected to a net-force nearest to equilibrium may then be selected as the second placement location.

Figure 4:
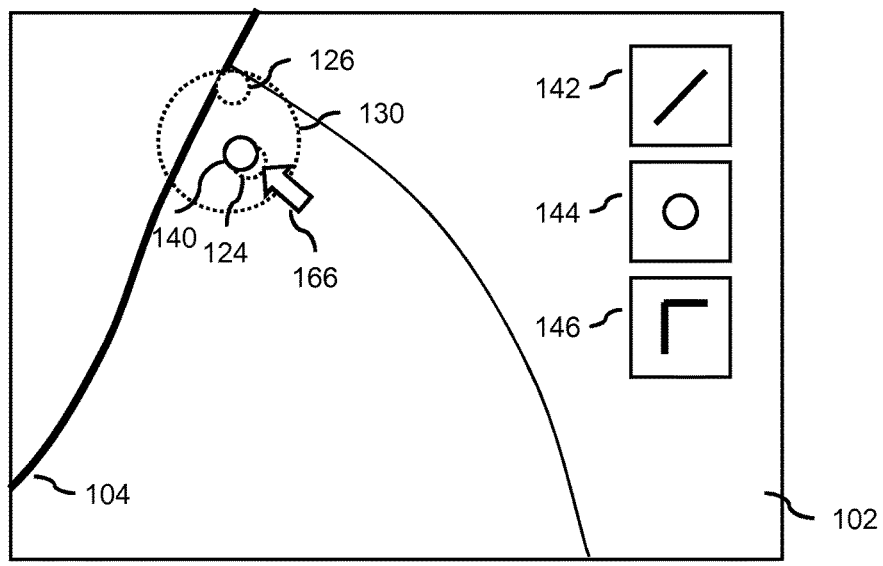
FIG. 4 shows a selection of the marker amongst different markers.

FIG. 4 illustrates another example of an operation of the system 100. Here, the system 100 is arranged for allowing the user to select the marker 140 amongst a plurality of different markers 142, 144, 146. FIG. 4 shows the markers being geometric primitives, i.e., a line segment 142, a circle 144 and a corner segment 146. It will be appreciated, however, that the markers may be any other type of graphical marker. FIG. 4 shows the result of the user having selected the circle as marker 140. The user input 160 may be arranged for receiving a selection command 163 from the user being indicative of a selection of the marker 140 amongst the plurality of different markers 142, 144, 146. The user may provide the selection command 163 by, e.g., clicking with the cursor 166 on a particular one of the plurality of markers, e.g., the circle 144. Moreover, the processor 180 may be arranged for configuring the image processing algorithm in dependence on the selected marker for being responsive to image portions which visually correspond to the selected marker 144. Thus, instead of being responsive to image portions that visually correspond to line segments, as previously shown in FIGS. 3a-3d, the image processing algorithm may be configured for being responsive to image portions that resemble circles of the particular diameter as the marker 140. In this respect, it is noted that configuring the image processing algorithm may comprise, e.g., modifying one or more parameters of the image processing algorithm, or selecting the image processing algorithm amongst a plurality of image processing algorithms.

Figure 5:
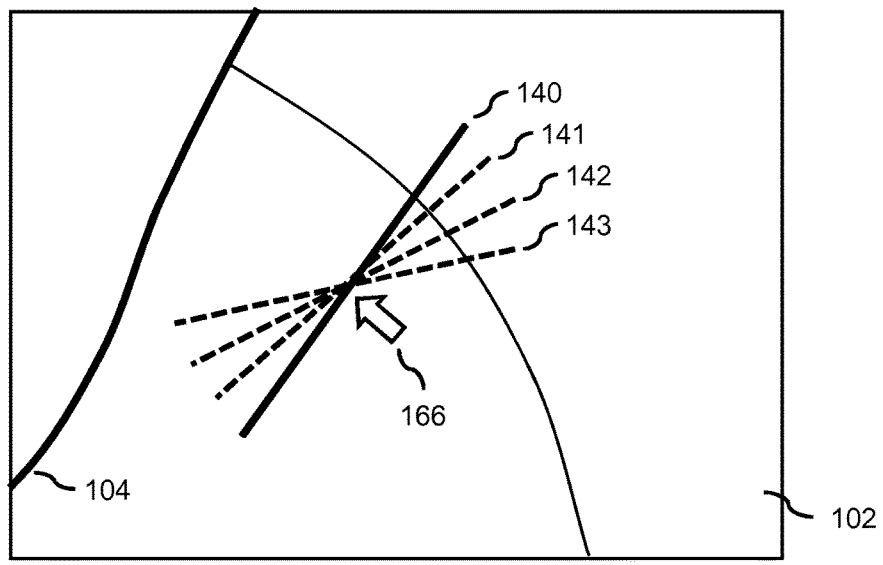
FIG. 5 shows the user determining an orientation of the marker.

FIG. 5 illustrates another example of an operation of the system 100. Here, the system 100 is arranged for allowing the user to determine an orientation of the marker 140. This is illustratively shown by the user selecting the orientation of the marker 140 amongst a plurality of orientations of the marker 141, 142, 143. For example, the system 100 may be arranged for allowing the user to determine the orientation of the marker 140 by allowing the user to rotate the marker around a center point of the marker 140. Moreover, the selection command 163 is further indicative of the orientation of the marker 140 as determined by the user, and the processor 180 may be further arranged for configuring the image processing algorithm in dependence on the orientation so as to be responsive to image portions which visually correspond to the selected marker 140 having said orientation. Any change in orientation of the marker is thus taken into account by the processor 180 configuring the image processing algorithm accordingly. For example, if the image processing algorithm comprises an edge detection filter, its filter coefficients may be modified to be responsive to edges running in the same direction as the orientation of the marker. Similarly, if the image processing algorithm comprises a template for performing template matching, the template may be rotated in accordance with the rotation of the marker 140.

Figure 6A:
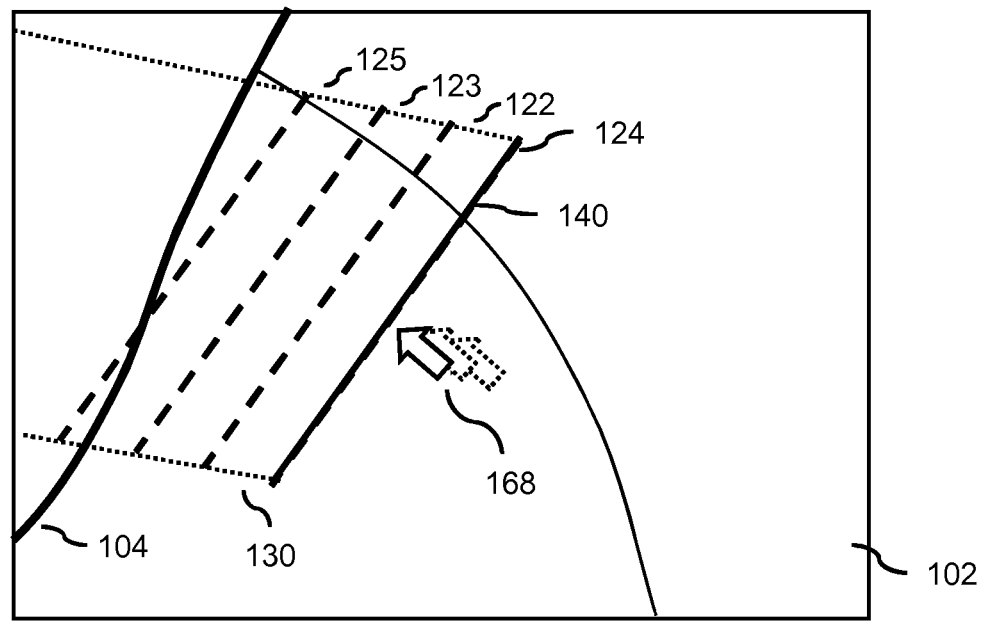
FIG. 6a shows the marker being placed with a cursor having a placement speed and placement direction at the time of placement of the marker.

FIG. 6*a* illustrates another example of an operation of the system 100. Here, the marker 140 is placed while the cursor 168 has a speed at the time of placement of the marker, henceforth referred to as placement speed, as well as a direction, henceforth referred to as placement direction. The placement speed and the placement direction are illustratively shown by the dotted cursors trailing the cursor 168. In this example, the user input 160 may be arranged for receiving the placement command from a user interface device being operable by the user. The user interface device may be, e.g., a mouse, a joystick, a touch screen, etc. The placement command may be further indicative of the placement direction associated with the user interface device or the cursor 168 at the time of providing the placement command. The placement command may be provided by, e.g., the user releasing the mouse button while operating the mouse to move the cursor 168 over the image 102. As shown in FIG. 6*a*, the placement direction may be the on-screen direction of a user interface element, such as the cursor 168, that is controlled by the user interface device. Alternatively, the placement direction may correspond to the physical direction of moving of the user interface device.

The processor 180 may be arranged for establishing a shape of the region 130 with respect to the first placement location 124 in dependence on the placement direction. In FIG. 6*a*, this is shown by the region 130 being shaped such that it extends predominantly in the placement direction with respect to the first placement location 124, instead of, e.g., being centered around the first placement location 124. Consequently, a plurality of potential placement locations 122, 123, 124, 125, corresponding to a non-depicted plurality of image portions within the region 130, are located predominantly in the placement direction with respect to the first placement location 124. The shape of the region 130 may be box-like. Similarly, the shape of the region 130 may be triangle-like or trapezoid-like, for example for widening the region 130 with increasing distance from the first placement location 124.

Alternatively, or in addition to the placement command being indicative of the placement direction, the placement command may be indicative of a placement speed of the user interface device or the cursor 168 at the time of providing the placement command. In this example, the processor 180 may be further arranged for establishing a size of the region 130 in dependence on the placement speed. For example, the size of the region 130 may be proportional to the placement speed, such that a high placement speed results in a large size of the region 130, and a low placement speed results in a small size of the region 130. As a result of the above, the user may use the user interface device or cursor 168 to 'throw' the marker 140 in the direction of the image portion that is to be annotated, with the marker 140 then 'snapping' to said image portion owing to the operation of the system 100.

The processor 180 may also be arranged for establishing the plurality of match degrees by establishing a plurality of detail measures being indicative of image detail present in the image 102 between, on the one hand, the first placement location 124, and on the other hand, the respective plurality of image portions, and weighting the plurality of match degrees with the plurality of detail measures for promoting image portions having less image detail in the image between them and the first placement location. As a result, the marker 140 'snaps' more easily to image portions that have less image detail between them and the first placement location 124, i.e., that have a clear path towards the first placement location 124 in terms of image detail. A physical analogy for this operation of the system 100 may be that of the image detail acting as a barrier or threshold for potential placement of the marker 140.

As an alternative, or in addition to the placement speed being used to determine the size of the region 130, the user input 160 may be arranged for receiving range data 165 from the user, the range data being indicative of the size of the region 130. The range data 165 may thus be obtained from a selection of the user that indicates the size of the region 130, e.g., by dragging a slider to indicate said size. Moreover, the processor 180 may be arranged for establishing the size of the region 130 in dependence on the range data 165. Thus, the user may also influence the size of the region 130 by providing said range data.

Figure 6B:
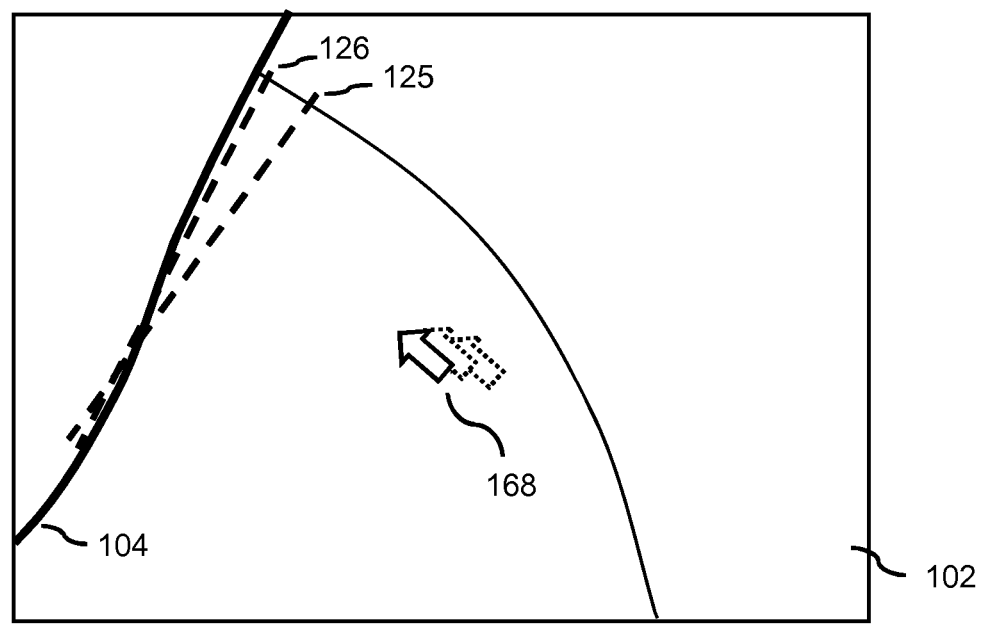
FIG. 6b shows the marker being adjusted to an image portion.

FIG. 6*b* illustrates another example of an operation of the system 100, in which the selecting of a second placement location 125 may be in accordance with the operation of the system 100 shown in FIG. 6*a* and described in reference thereto. Here, the selected second placement location 125 is shown to have a corresponding, yet non-depicted, image portion that amongst the plurality of placement locations 122, 123, 124, 125 as shown in FIG. 6*a* most resembles the marker 140. However, the second placement location 125 is not in perfect alignment with the pectoral muscle 104. The processor 180 may be arranged for placing the marker 140 by adjusting, either during or before the placing step, the shape, the orientation or the size, or a combination thereof, of the marker 140 in order to match the marker 140 to the image portion that is to be annotated, i.e., the pectoral muscle 104, which is only partially located at the second placement location 125. In this particular example, the marker 140 is rotated to better match the orientation of the pectoral muscle 104, and subsequently placed after said rotation. Effectively, this results in the second placement location 125 being adjusted in accordance with the adjustment of the marker 140, resulting in a rotated second placement location 126 with respect to the second placement location 125.

For adjusting the marker 140 with respect to the image portion at the second placement location, various techniques from the fields of image processing and image analysis may be used. For example, the Hough transform may be used to determine the orientation of the pectoral muscle 104, with the marker 140 then being rotated accordingly. In the case that the marker 140 is a computer graphics model, e.g., comprising vertices and faces, certain features of the image portion may be detected by, e.g., using an image segmentation or image analysis algorithm, and the marker 140 may be deformed in order to fit the detected features of the image portion, i.e., the marker 140 may be a deformable marker.

In general, and as shown in FIG. 1, the user input 160 may be arranged for receiving type data 163, the type data being indicative of a type of image portion to be annotated in the image, and the processor may be further arranged for configuring the image processing algorithm in dependence on the type data so as to be responsive to image portions which visually correspond to the type of image portion and the marker. Therefore, the user may select a type of image portion that he wishes to annotate in the image, e.g., by clicking on an example or template of the image portion. The image processing algorithm may then be configured to be equally responsive to the selected type of image portion and the marker, but more responsive to an image portion that resembles both the selected type of image portion and the marker. The type of image portion may be automatically selected by the system, e.g., when it is known what type of image portion is to be annotated. For example, when annotating anatomic landmarks in 2D mammograms, it is known that the type of image portion is typically the mammilla or the inframammary fold. Hence, the image processing algorithm may be configured to be responsive to either type.

The processor may also be arranged for establishing the second placement location using techniques from the field of mathematical optimization. In particular, the image portion that is to be annotated may be any one of all or substantially all image portions within a region or the entire image. Determining a match degree for all of the image portions may lead to a high computational complexity. In order to avoid this high computational complexity, the processor may be arranged for applying, e.g., a gradient descent or similar optimization method, in which the match degree is used as a function that is to be optimized, with the variables in said function being the location within the region. Thus, the processor may iteratively arrive at the second placement location, this location being a result obtained by the optimization method. Therefore, an exhaustive calculation of the match degrees for all of the image portions is avoided. It will be appreciated that in this case, the region may be established by setting or adjusting one or more parameters in the optimization method that relate to, e.g., the number of iterations or the distance to the first placement location.

In general, it is noted that the system may be configured such that, in case the second placement location inadvertently does not correspond to an intended one, i.e., it does not correspond to the image portion that is to be annotated, the user may correct the second placement location by providing a new placement command for requesting the system to again establish the second placement location, or by manually placing the marker without requesting the system to further refine the placement of the marker.

It is further noted that the plurality of image portions may be constituted by a first image portion located at the first placement location and a further image portion located at a further placement location, with the system thus comparing the match degree between the marker and said image portions and placing the marker at one of both image portions, i.e. the image portion that yields the highest match degree. The second placement location may be the further placement location, but may equally be the first placement location if the match degree between the marker and the first image portion is the highest match degree.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or to be used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for interactive annotation of an image, comprising:

a user input that receives a placement command from a user, the placement command being indicative of a first placement location of a marker in the image, the placement command being obtained by the user using a user interface device to move the marker over the image; and a processor that:
applies an image processing algorithm to a region in the image, the region being based on the first placement location, the image processing algorithm determining a plurality of match degrees between the marker and a plurality of image portions within the region, wherein the match degrees are determined based on the image processing algorithm providing a distinct output for image portions that visually correspond to the marker,
determines a second placement location in dependence on the plurality of match degrees and the respective plurality of image portions for matching the marker to the region in the image, and
places the marker at the second placement location in the image.

2. The system of claim 1, wherein:
the user input receives a selection command from the user, the selection command being indicative of a selection of the marker amongst a plurality of different markers; and
the processor configures the image processing algorithm in dependence on the selected marker so as to be responsive to image portions that visually correspond to the selected marker.

3. The system of claim 2, wherein the selection command is further indicative of an orientation of the selected marker as determined by the user, and wherein the processor configures the image processing algorithm in dependence on the orientation so as to be responsive to image portions that visually correspond to the selected marker having said orientation.

4. The system of claim 1, wherein:
the user input receives type data, the type data being indicative of a type of image portion to be annotated in the image; and
the processor configures the image processing algorithm in dependence on the type data so as to be responsive to image portions that visually correspond to the type of image portion and the marker.

5. The system of claim 1, wherein the processor determines the second placement location by adjusting at least one of: a shape, an orientation and a size of the marker for matching the marker to an image portion at the second placement location.

6. The system of claim 1, wherein the processor determines the plurality of match degrees by:
establishing a plurality of distances between the first placement location, and the respective plurality of image portions; and
weighting the plurality of match degrees with the plurality of distances for promoting image portions that are located nearer to the first placement location.

7. The system of claim 1, wherein the processor determines the plurality of match degrees by:
establishing a plurality of detail measures being indicative of image detail present in the image between the first placement location, and the respective plurality of image portions; and weighting the plurality of match degrees with the plurality of detail measures for promoting image portions having less image detail in the image between them and the first placement location.

8. The system of claim 1, wherein the processor determines the second placement location by using a force-based model comprising the plurality of match degrees as attracting forces.

9. The system of claim 1, wherein the user input receives range data from the user, the range data being indicative of a size of the region, and the processor establishes the size of the region in dependence on the range data.

10. The system of claim 1, wherein the placement command is further indicative of a placement direction, and wherein the processor establishes a shape of the region with respect to the first placement location in dependence on the placement direction.

11. The system of claim 10, wherein the placement command is further indicative of a placement speed at the time of providing the placement command, and wherein the processor establishes a size of the region in dependence on the placement speed.

12. A workstation comprising the system according to claim 1.

13. An imaging apparatus comprising the system according to claim 1.

14. A method of enabling interactive annotation of an image, comprising:
receiving a placement command from a user, the placement command being indicative of a first placement location of a marker in the image, the placement command being obtained by the user using a user interface device to move the marker over the image;
applying an image processing algorithm to a region in the image, the region being based on the first placement location, the image processing algorithm being configured for determining a plurality of match degrees between the marker and a plurality of image portions within the region, wherein the match degrees are determined based on the image processing algorithm providing a distinct output for image portions that visually correspond to the marker;
determining a second placement location in dependence on the plurality of match degrees and the respective plurality of image portions for matching the marker to the region in the image; and
placing the marker at the second placement location in the image.

15. A non-transitory computer-readable medium comprising a program that, when executed by a processing system, causes the processing system to:
receive a placement command from a user, the placement command being indicative of a first placement location of a marker in the image, the placement command being obtained by the user using a user interface device to move the marker over the image;
apply an image processing algorithm to a region in the image, the region being based on the first placement location, the image processing algorithm being configured for determining a plurality of match degrees between the marker and a plurality of image portions within the region, wherein the match degrees are determined based on the image processing algorithm providing a distinct output for image portions that visually correspond to the marker;

determine a second placement location in dependence on the plurality of match degrees and the respective plurality of image portions for matching the marker to the region in the image; and place the marker at the second placement location in the image.

16. The medium of claim 15, wherein the program causes the processing system to:

receive a selection command from the user, the selection command being indicative of a selection of the marker amongst a plurality of different markers; and configure the image processing algorithm in dependence on the selected marker so as to be responsive to image portions that visually correspond to the selected marker.

17. The medium of claim 16, wherein the selection command is further indicative of an orientation of the selected marker as determined by the user, and wherein the program causes the processing system to configure the image processing algorithm in dependence on the orientation so as to be responsive to image portions that visually correspond to the selected marker having said orientation.

18. The medium of claim 15, wherein the program causes the processing system to:

receive type data, the type data being indicative of a type of image portion to be annotated in the image; and configure the image processing algorithm in dependence on the type data so as to be responsive to image portions that visually correspond to the type of image portion and the marker.

19. The medium of claim 15, wherein the program causes the processing system to determine the second placement location by adjusting at least one of: a shape, an orientation and a size of the marker for matching the marker to an image portion at the second placement location.

20. The medium of claim 15, wherein the program causes the processing system to determine the plurality of match degrees by:

establishing a plurality of distances between the first placement location, and the respective plurality of image portions; and weighting the plurality of match degrees with the plurality of distances for promoting image portions that are located nearer to the first placement location.

* * * * *